United States Patent [19]

Stuttle

[11] Patent Number: 5,628,979
[45] Date of Patent: May 13, 1997

[54] REAGENT FOR TUMOR IMAGING AND THERAPY

[75] Inventor: Alan W. J. Stuttle, Banstead, Great Britain

[73] Assignee: Antisoma Limited, London, England

[21] Appl. No.: 190,130

[22] PCT Filed: Aug. 6, 1992

[86] PCT No.: PCT/GB92/01458

§ 371 Date: Jun. 13, 1994

§ 102(e) Date: Jun. 13, 1994

[87] PCT Pub. No.: WO93/02708

PCT Pub. Date: Feb. 18, 1993

[30] Foreign Application Priority Data

Aug. 6, 1991 [GB] United Kingdom .................. 9116925

[51] Int. Cl.$^6$ ........................... A61K 51/00; A61M 36/14
[52] U.S. Cl. ........................ 424/1.11; 424/1.69; 424/9.1; 530/300; 530/324; 530/325; 530/326; 530/327; 530/328; 530/329; 530/330
[58] Field of Search ............... 514/12–18; 530/324–330, 530/300; 424/1.11, 1.69, 9.1; 534/10, 14

[56] References Cited

U.S. PATENT DOCUMENTS

| | | | |
|---|---|---|---|
| 4,691,006 | 9/1987 | Stevens | 530/324 |
| 4,767,842 | 8/1988 | Stevens | 530/324 |
| 5,382,569 | 1/1995 | Cody et al. | 530/329 |

FOREIGN PATENT DOCUMENTS

| | | | |
|---|---|---|---|
| 0359347 | 3/1990 | European Pat. Off. | A61K 47/00 |
| 0428266 | 5/1991 | European Pat. Off. | A61K 47/00 |
| 0527056 | 2/1993 | European Pat. Off. | |
| 9009799 | 9/1990 | WIPO | A61K 37/02 |
| WO9015818 | 12/1990 | WIPO | C07K 15/08 |
| 9302708 | 2/1993 | WIPO | A46K 47/48 |

OTHER PUBLICATIONS

R Markarem and Humphries, MJ (1991), Biochemical Society Transactions (1991)19, 380S LDV: A Novel Cell Adhesion Motif Recognized by the Integrim $L_4B_1$.

Shimizu et al. (1990), Journal of Immunology, vol. 145 pp. 59–67, Costimulation of Proliferative Responses of Resting CD4+ T Cells by the Interaction of VLA–4 and VLA–5 with Fibronectin or VLA–6 with Laminin.

Mould et al. (1991) Journal of Biological Chemistry, vol. 266, #6 Feb. 25, pp. 3579–3585. The CS5 Peptide is a Second Site in the III CS Region of Fibronectin Recognized by the Integrin $L_4B_1$.

Wayner and Kovach (1992). The Journal of Cell Biology, vol. 116, #2, Jan. (1992) pp. 489–497. Activation–Dependent Recognition by Hematopoietic Cells of the LDV Sequence in the V Region of Fibronectin.

Guan and Hynes, Cell vol. 60, pp. 53–61 (1990). Lymphoid Cells Recognize an Alternatively Spliced Segment of Fibronectin via the Integrin Receptor $2_4B_1$.

Komoriya et al. (1991) vol. 266, #23, pp. 15075–15079, The Journal of Biological Chemistry. The Minimal Essential Sequence for a Major Cell Type–Specific Adhesion Site (CSI) Within the Alternatively Spliced Type III Connecting Segment Domain of Fibronectin Is Leucine–Asparatic Acid—Valine.

Krystek et al (1989) International Journal of Peptide and Protein Research, vol. 34, pp. 52–55. Cleavage of a Model Peptide at its Glycine Residue by Alkaline Mercuric Oxycyanide.

Lebien et al (1982). vol 129, No. 5. Antibody Affinity May Influence Antigenic Modulation of the Common Acute Lymphoblastic Leukemia Antigen In Vitro. pp. 2287–2292. Journal of Immunology.

Mould et al. (1990) vol. 265, No. 7, Journal of Biological Chemistry pp. 4020–4024. Affinity Chromatographic Isolation of the Melanoma Adhesion Receptor for the IIICS Region of Fibronectin and Its Identification as the Integrin $L_4B_1$.

Mathew Van Holde. Biochemistry, Chapter 5:Introduction to Proteins:The Primary Level of Protein Structure, pp. 139–141. ©1990.

*Primary Examiner*—John Kight
*Assistant Examiner*—Dameron L. Jones
*Attorney, Agent, or Firm*—Fay, Sharpe, Beall, Fagan, Min-

[57] ABSTRACT

Novel oligopeptides are disclosed for in vivo tumor imaging and therapy. The novel oligopeptides are oligopeptides containing from 4 to 50 peptide units containing as a characteristic triplet therein the amino acid sequence leu-asp-val (LDV), which triplet provides the oligopeptide with a strong in vivo binding affinity for LDV binding sites on tumors and other tissues. For diagnostic purposes the oligopeptides are labelled with a radioactive label, e.g. $^{125}I$, whilst for therapeutic purposes the oligopeptides are chemically linked to or conjugated with a cytotoxin, such as the ricin A-chain.

31 Claims, 4 Drawing Sheets

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 25
( B ) TYPE: Amino Acid
( C ) STRANDEDNESS: Single
( D ) TOPOLOGY: Linear ( i i ) MOLECULE TYPE: Peptide ( x ) SEQUENCE DESCRIPTION: SEQ ID NO: 1:

Asp Glu Leu Pro Gln Leu Val Thr Leu Pro
 1               5                   10

His Pro Leu Leu His Gly Pro Glu Ile Leu
                 15                  20

Asp Val Pro Ser Thr
                25

( 2 ) INFORMATION FOR SEQ ID NO:2:

( i ) SEQUENCE CHARACTERISTICS:
( A ) LENGTH: 13
( B ) TYPE: Amino Acid
( C ) STRANDEDNESS: Single
( D ) TOPOLOGY: Linear ( i i ) MOLECULE TYPE: Peptide ( x ) SEQUENCE DESCRIPTION: SEQ ID NO: 2:

Tyr Gly Gly Leu Asp Val Gly Leu Asp Val
 1               5                   10

Gly Gly Tyr ( 2 ) INFORMATION FOR SEQ ID NO:3:

( i ) SEQUENCE CHARACTERISTICS:
        ( A ) LENGTH: 12
        ( B ) TYPE: Amino Acid
        ( C ) STRANDEDNESS: Single
        ( D ) TOPOLOGY: Linear ( i i ) MOLECULE TYPE: Peptide ( x ) SEQUENCE DESCRIPTION: SEQ ID NO: 3:

```
Leu His Gly Pro Glu Ile Leu Asp Val Pro
 1               5                    10

Ser Thr
```

( 2 ) INFORMATION FOR SEQ ID NO:4:

( i ) SEQUENCE CHARACTERISTICS:
        ( A ) LENGTH: 25
        ( B ) TYPE: Amino Acid
        ( C ) STRANDEDNESS: Single
        ( D ) TOPOLOGY: Linear ( i i ) MOLECULE TYPE: Peptide ( x ) SEQUENCE DESCRIPTION: SEQ ID NO: 4:

```
Asp Glu Leu Pro Gln Leu Val Thr Leu Pro
 1               5                    10

His Pro Asn Leu His Gly Pro Glu Ile Leu
                 15                   20

Asp Val Pro Ser Thr
                 25
```

( 2 ) INFORMATION FOR SEQ ID NO:5:

( i ) SEQUENCE CHARACTERISTICS:
        ( A ) LENGTH: 31
        ( B ) TYPE: Amino Acid
        ( C ) STRANDEDNESS: Single
        ( D ) TOPOLOGY: Linear ( i i ) MOLECULE TYPE: Peptide ( x ) SEQUENCE DESCRIPTION: SEQ ID NO: 5:

```
Lys Lys Thr Asp Glu Leu Pro Gln Leu Val
 1               5                    10

Thr Leu Pro His Pro Asn Leu His Gly Pro
                 15                   20

Glu Ile Leu Asp Val Pro Ser Thr Val Gln
                 25                   30

Lys
```

( 2 ) INFORMATION FOR SEQ ID NO:6:

( i ) SEQUENCE CHARACTERISTICS:
        ( A ) LENGTH: 12
        ( B ) TYPE: Amino Acid
        ( C ) STRANDEDNESS: Single
        ( D ) TOPOLOGY: Linear ( i i ) MOLECULE TYPE: Peptide ( x ) SEQUENCE DESCRIPTION: SEQ ID NO: 6:

```
His His Leu Gln Leu Leu Lys Gln Leu Leu
```

-continued

```
        1                      5                          1 0
Asp Val
```

REAGENT FOR TUMOR IMAGING AND THERAPY

FIELD OF INVENTION

This invention relates to in vivo tumor imaging and therapy, and more particularly to a novel reagent for use therein, diagnostic and therapeutic compositions containing that reagent, and methods of tumor imaging and therapy utilising the reagent.

X is glycine, leucine or glutamic acid, and Y is serine or valine, represents a minimum recognition sequence within the CS1 site of the fibronectin for the integrin $\alpha_4\beta_1$. Inter alia, those studies utilised synthetic CS1 and KKT-CS1-VQK peptides, viz:

CS1

```
D    E    L    P    Q    L    V    T    L    P    H    P    N    L    H    G    P
asp—glu—leu—pro—gln—leu—val—thr—leu—pro—his—pro—asn—leu—his—gly—pro—
E    I    L    D    V    P    S    T (SEQ ID NO. 4)
glu—ile—leu—asp—val—pro—ser—thr
```

KKT-CS1-VQK

```
K    K    T    P    E    L    P    Q    L    V    T    L    P    H    P    N    L
lys—lys—thr—asp—glu—leu—pro—gln—leu—val—thr—leu—pro—his—pro—asn—leu—
H    G    P    E    I    L    D    V    P    S    T    V    Q    K (SEQ ID NO. 5)
his—gly—pro—glu—ile—leu—asp—val—pro—ser—thr—val—gln—lys
```

BACKGROUND INFORMATION AND PRIOR ART

In the cause of improving the diagnosis and treatment of cancer numerous attempts have been made to target imaging agents, e.g. radioactive isotopes, and therapeutic reagents onto tumors in vivo using anti-tumor monoclonal antibodies, Mabs, see for example published International Applications WO 89/00583 and WO 90/09197. Because of the size of the average Mab, diffusion rates of, for example, a radio-labelled antibody to the site of a tumor are very low, and the same applies to conjugates formed from a cytotoxic reagent and an anti-tumor antibody.

Tumor imaging and therapy using Mabs is therefore inherently a slow process, often taking several hours, whereas ideally one would like to have the process complete in minutes, rather than hours, particularly in the case of tumor imaging and diagnosis.

In J. Immunol., 145, No, 1, 59–67, 1990, Shimizu et al have reported on the co-stimulation of proliferative responses of resting CD4U⁺T-cells by the interaction of the extracellular matrix (ECM) proteins fibronectin (FN) and laminin (LN) with the VLA integrins VLA-4 and VLA-5 (in the case of fibronectin) or VLA-6 (in the case of laminin) expressed by resting human T-lymphocytes, and have shown inter alia that the 12-amino acid peptide (SEQ ID NO. 3)

```
L    H    G    P    E    I    L    D    V    P    S    T
(leu—his—gly—pro—glu—ile—leu—asp—val—pro—ser—thr)
``` is an effective T-cell adhesion inhibitor and an effective blocking agent for OKT3/FN T-cell proliferation, but does not go beyond a mere investigation into the role of cell adhesion molecules (CAMs) in T-cell recognition and activation. Thus, Shimizu et al suggest no practical outcome or industrial utility resulting from their investigations.

In J. Biol. Chem., 266, No. 6, 3579–3585, 1991, Mould et al have reported their studies of the inhibition of the interaction of the integrin heterodimer $\alpha_4\beta_1$ with the CS1 and CS5 sites in the IIICS region of fibronectin, which interaction is believed to play an important role in melanoma cell adhesion, and have shown that the tripeptide X-asp-Y, where but again no consequential commercial utility is suggested for such LDV (leu-asp-val) containing peptides.

Subsequent studies of similar kind confirming the significance of the LDV triplet as the minimum recognition site for the $\alpha_4\beta_1$ integrin, as opposed to the RGDS sequence which constitutes the minimum recognition site for the $\alpha_5\beta_1$ integrin, those two minimum recognition sites occurring in different domains of the fibronectin (FN) molecule, viz. the alternatively spliced type III connecting segment (IIICS) and the central cell binding domain respectively, are reported by Komoriya et al in J. Biol. Chem., 266, No. 23, 15075–15079, 1991, but published after the present priority date.

Earlier studies into the cell binding activity of fibronectin are reported by Pierschbacher and Ruoslahti (Nature, 309, 30–33, 1984) and by Kloczewiak et al in Biochemistry 28, 2915–2919, 1989. Pierschbacher et al recognize the importance of the RGDS sequence as a recognition site in the cell adhesion activity of fibronectin, but report that they were unable to obtain any inhibition of cell adhesion using either soluble fibronectin or by peptides not containing the RGDS sequence. Similarly Kloczewiak et al, investigating the essential role of the terminal region of the fibrinogen γ-chain in the interaction of human fibrinogen with activated platelets, showed that the synthetic dodecapaptide:

(SEQ ID NO. 6)

```
H    H    L    Q    L    L    K    Q    L    L    D    V
his—his—leu—gln—leu—leu—lys—gln—leu—leu—asp—val
``` being an analogue of the γ400–411 FN residue, and containing the LDV triplet, achieved 50% inhibition of fibrinogen binding to activated platelets, but only at concentrations greater than 500 μM.

In contrast to both Shimizu et al and Mould et al, EP-A-0428266 identifies as potential anti-cancer agents, peptides based on the functional domains of fibronectin, more particularly the cell binding domains and the heparin binding domains, amino acid residues 1239–1515 and 1690–1960 respectively (EP-A-0428266, SEQ ID Nos. 2 and 3). According to EP-A-0428266, these fibronectin fragments show anti-cancer activity in mice by inhibiting metastasis, and may be used singly or in the form of a chimeric peptide comprising both sequences linked by a linker, e.g. a methionine residue, EP-A-0428266 SEQ ID No. 4. In either event, the peptide fragment is of substantial size: 277 amino acid residue in the case of the cell binding domain FN fragment, and 271 in the case of the heparin binding FN fragment, making a total of 549 amino acid residues in the chimeric peptide. Such fragments are therefore still of substantial size compared to the oligopeptides used in the present invention, and can be expected still to show many of the disadvantages of the Mab based anticancer agents, namely low diffusion and clearance rates. Not only that, but none of the FN fragments disclosed as anti-cancer agents in EP-A-0428266 contain the amino acid triplet which is characteristic of the oligopeptides used in accordance with the present invention, that is to say the leu-asp-val (LDV) triplet.

More recently, in published International Patent Application WO 90/15858, the present inventor has disclosed novel peptides comprising an RGD sequence (i.e. the sequence: arg-gly-asp) primarily for in vivo thrombus imaging, but also potentially useful for in vivo tumor imaging and therapy, and capable of binding to tumors in vivo via RGD binding sites on the surface of the tumor. In the case of thrombus imaging the peptide binds to RGD recognition and binding sites in the GPIIb/IIIa (glycoprotein-fibrinogen receptor) complex present on the membrane surface of activated platelets, and which contain the fibrinogen binding domains and which are involved in the aggregation of the activated platelets to form the thrombus.

OBJECTS OF THE PRESENT INVENTION

The present invention seeks to overcome the above-mentioned disadvantages of monoclonal antibody (Mab) based cytotoxic and diagnostic reagents by providing novel oligopeptide based reagents having specific binding properties to tumor associated binding sites, and which are rapidly transported to the tumor site following injection, with equally rapid clearance of unbound reagent from the body following administration, thus considerably reducing treatment times and reducing the effective dosage of potentially highly toxic reagents, whether administered for diagnostic or therapeutic purposes.

Further objects of the present invention are to provide tumor diagnostic and therapeutic compositions containing such reagents, and methods of diagnostically imaging or treatment of tumors using such reagents.

SUMMARY OF PRESENT INVENTION

In accordance with the present invention the above objectives are achieved using a synthetic oligopeptide of from 4 to about 50 peptide units and containing the sequence

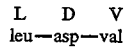

referred to herein as the LDV sequence, which sequence binds the oligopeptide in vivo to LDV binding sites on the tumor.

Because of their relatively small size, such oligopeptides diffuse rapidly throughout the body and, equally importantly, are rapidly cleared from the body by ordinary metabolic and/or excretory processes, leaving behind only bound oligopeptide bound to the tumour or to other tissue structures containing an LDV binding site. This rapid clearance of unbound oligopeptide from the body is particularly important in the case of tumor imaging using a radio-labelled oligopeptide, since it permits visualization of local concentrations of bound radio-labelled oligopeptide by conventional radiological techniques within a relatively short period of time following intravenous administration of the diagnostic reagent, i.e. the radio-labelled oligopeptide.

The rapid clearance of unbound oligopeptide from the body is also invaluable in reducing possible toxic side effects of cytotoxic drugs used in tumor therapy regimes and administered, in accordance with the concepts of this invention, as a conjugate formed from the cytotoxic reagent and an oligopeptide of from 4 to about 50 peptide units and containing the sequence

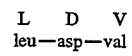

BRIEF DESCRIPTION OF DRAWINGS

The binding capacity of radio-labelled peptides according to the invention to tumor cells, both in vitro and in vivo is illustrated by the accompanying drawings, in which.

DETAILED DESCRIPTION

Figure 1:
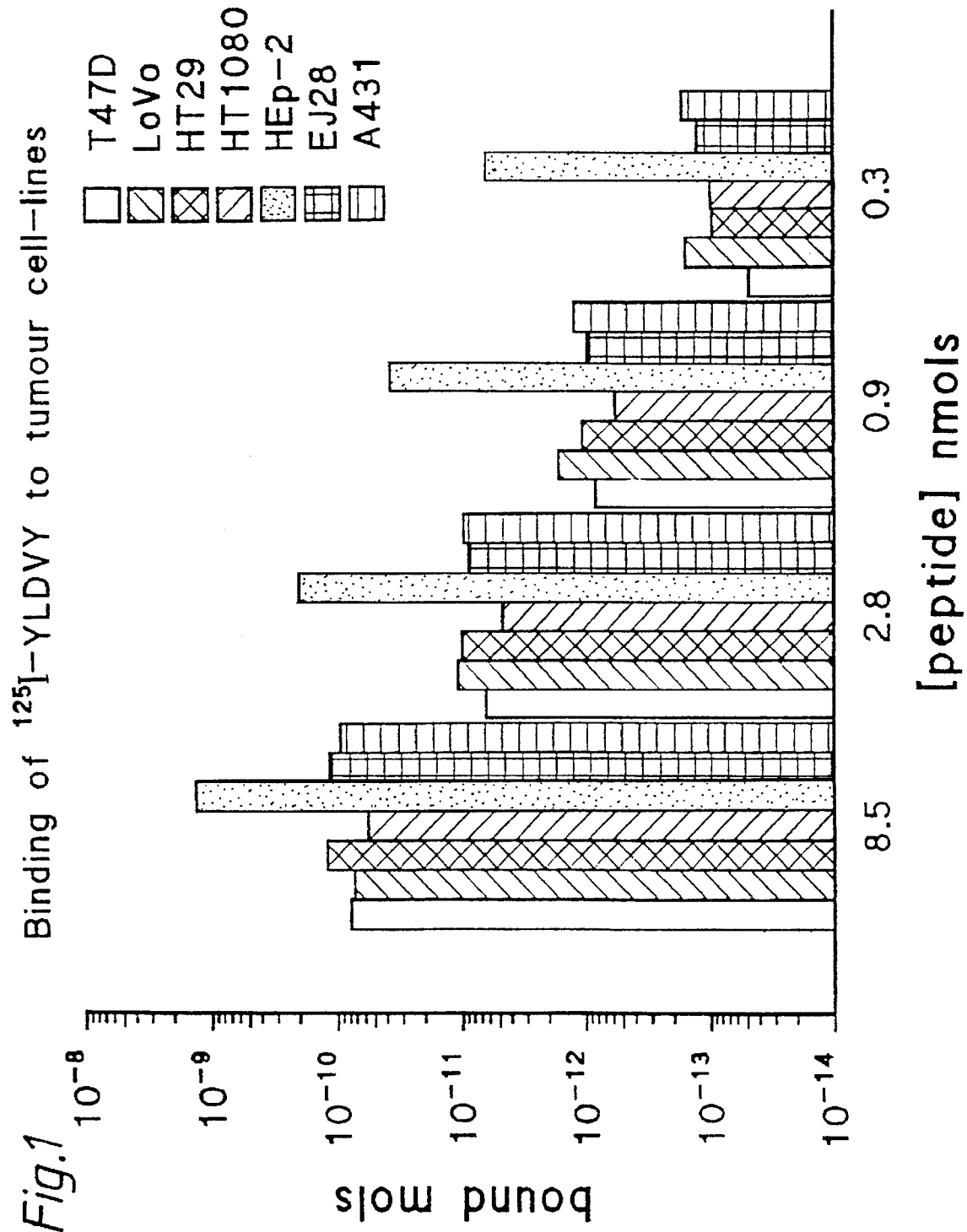
FIG. 1 is a bar chart illustrating the binding capacity of the radio-labelled peptide $^{125}$I-YLDVY to tumor cells from cell lines T47D, LoVo, HT29, HT1080, HEp-2, EJ28 and A431, in vitro.

In accordance with this invention, therefore, there are provided diagnostic and therapeutic reagents, primarily for in vivo tumor imaging and therapy, but also useful in targeting other pathological tissues containing an LDV-binding site, such reagents comprising an oligopeptide of from 4 to about 50 peptide units and containing as a triplet therein the sequence

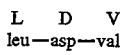

and to which oligopeptide there is attached either a radioactive label or cytotoxin.

As to the actual size of the oligopeptide used in accordance with the present invention, this will be determined largely by economic considerations: generally in the construction of oligopeptides on a peptide synthesizer cost is directly proportional to length. For synthetic oligopeptides therefore, 50 peptide units represents the maximum chain length that is likely to be viable economically, although in practice very much shorter chain lengths are the more likely, e.g. from 4 to 30, down to 4 to 20 or 4 to 15, or as little as 4 to 10. Particularly preferred sequences are the CS1 sequence of fibronectin, i.e. a 25-unit oligopeptide having the sequence SEQ ID No. 1, and sub-units thereof containing the LDV triplet. Other suitable oligopeptides include the five unit peptide:

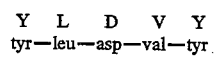

the nine unit peptide:

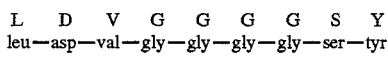

and the thirteen unit peptide: SEQ ID No. 2.

The CS1 sequence of fibronectin, SEQ ID No. 1, is known to bind to the cell adhesion molecule (CAM) VLA-4 expressed in vitro by many tumour cells and by resting CD4$^+$T-cells (see Shimizu et al above). It is now established that the CS1 sequence of fibronectin and other LDV-containing peptides bind strongly to tumor cells in vivo, thus providing a method of targeting imaging or therapeutic reagents onto those cells.

A variety of different techniques are available for attaching a radioactive label to the oligopeptide, and a variety of different labels are available for this purpose. Amongst those there may be mentioned, in particular: technetium-99m, iodine-123 or iodine-125 and indium-111. In order to attach the label (or for that matter, a cytotoxic reagent) the oligopeptide will usually be provided with a reactive terminal amino acid residue such as a terminal tyrosine, histidine, lysine or cysteine residue. When using $^{99m}$Tc as the label this may be attached via a cysteine residue, $^{125}$I via a tyrosine residue, and $^{111}$In via a lysine residue. Attachment of $^{125}$I to an oligopeptide via a tyrosine residue is described in WO 90/15818, and the same procedure may be used herein. Other suitable techniques are described in Science 220, 613–615; Int. J. Nucl. Med. Biol., 12, 3–8; J. Nucl. Med., 26, 293–299 and J. Nucl, Med., 27, 685–693, incorporated herein by reference.

In the alternative, there may be attached to the oligopeptide, in place of the radioactive label, a cytotoxic agent, such as ricin or a derivative or component thereof, particularly the ricin A-chain. Methods of attaching a cytotoxic agent, such as ricin A-chain, to the oligopeptide will depend on the particular cytotoxin to be used, and the functional groups contained therein and by means of which the cytotoxin can be chemically coupled to functional groups in the oligopeptide, either directly or by means of a di-functional coupling agent. The choice of coupling agent or method will be well within the abilities of the ordinary person skilled in the art, see for example WO 88/00583 incorporated herein by reference, so also will be other suitable cytotoxic reagents besides the ricin and ricin derivatives already mentioned.

The detailed preparation of radioactively labelled peptides according to this invention is illustrated by the following example:

EXAMPLE

Preparation of radioactively labelled $^{125}$I-YLDVY, $^{125}$I-LDVGGGGSY, and $^{125}$I-YGGLDVGLDVGGY (SEQ ID NO. 2)

The oligopeptides YLDVY, LDVGGGGSY (corresponding amino acid sequences, see above), and YGGLDVGLDVGGY (amino acid sequence, see SEQ ID No. 2), were synthesised by standard procedures using an automatic peptide synthesizer.

Iodogen tubes were prepared by dissolving Iodogen (1,3, 4,6-Tetrachloro-3a,6a-diphenylglycouril) in chloroform at a concentration of 1 mg.ml$^{-1}$. Aliquots of 50 µl (50 µg Iodogen) were dispensed into polypropylene cryo-tubes and the chloroform evaporated to dryness. These tubes were then stored desiccated at −20° C. until required.

Prior to radio-labelling the peptides were dissolved in phosphate buffered saline (PBS) at a concentration of 50 µg.ml$^{-1}$.

Iodogen tubes were equilibrated to room temperature before the addition of 200 µl peptide solution and 1–10 µl of $^{125}$I (in aqueous solution). The reaction mixture was then left for 15 minutes at room temperature with occasional shaking. Following the incubation period the reaction mixture was removed and passed through a Sephadex G10 column which had been equilibrated with PBS. The column, which separates radio-labelled peptide from free iodine was eluted with PBS and 2 ml fractions collected. Radioactivity in the fractions was measured and the eluted peptides, represented by the first radioactive peak from the column, collected and stored at 4° C. until required.

At this point, it may be mentioned that, in accordance with the usual convention on the representation of labelled peptides, the representation $^{125}$I-YLDVY, for example, merely indicates that the peptide YLDVY has been labelled with $^{125}$I. It is not intended to indicate either the position of attachment of the label or the actual number of radioactive iodine atoms attached to the peptide molecule.

The capacity of the radioactively labelled peptides to bind to tumor cells in vitro and in vivo is illustrated by the following experiments, the results of which are illustrated in the accompanying drawings.

EXPERIMENT 1

Figure 2:
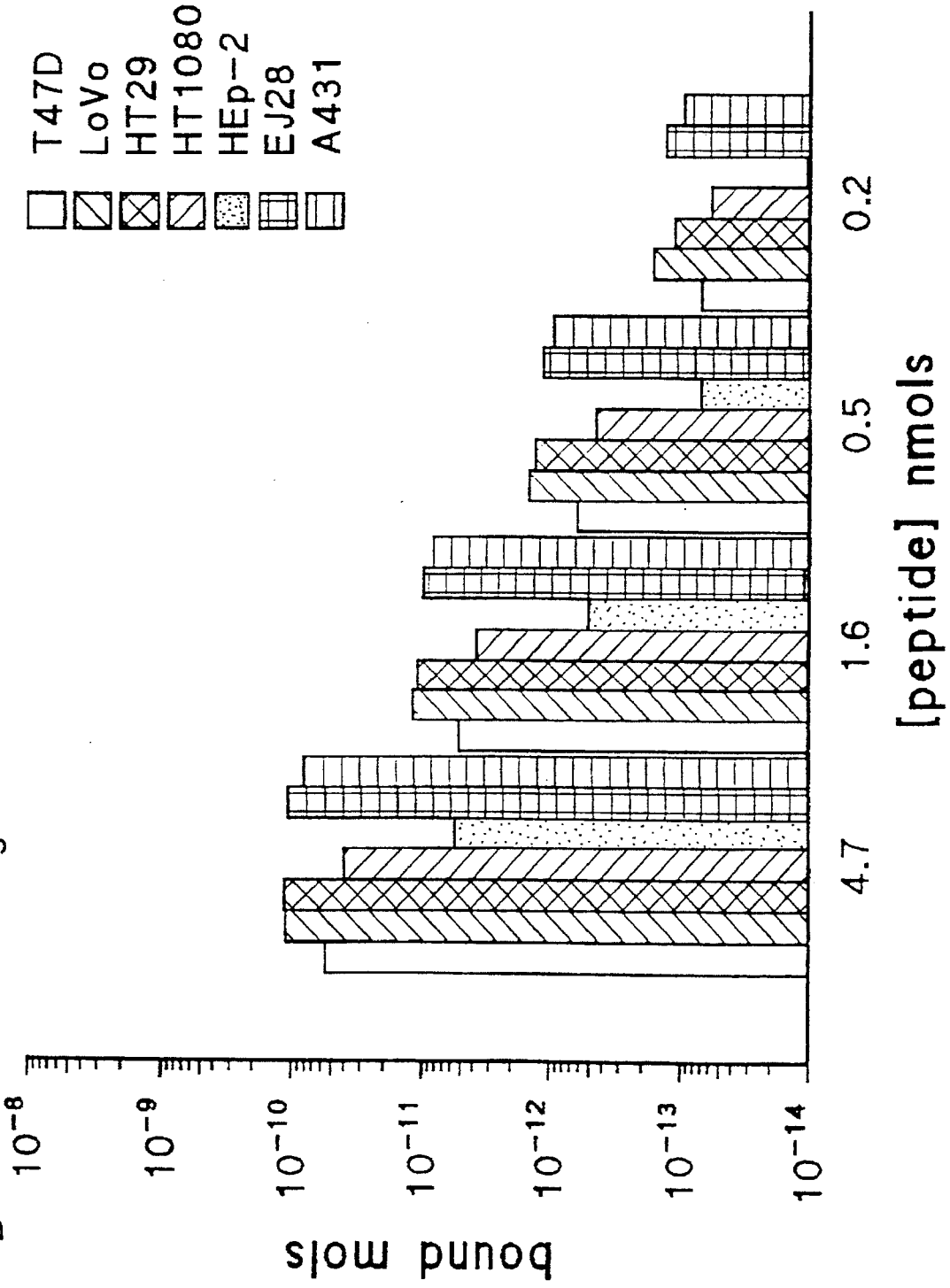
FIG. 2 presents similar data in respect of the radio-labelled peptide $^{125}$I-YGGLDVGLDVGGY (SEQ ID NO. 2)
Figure 3:
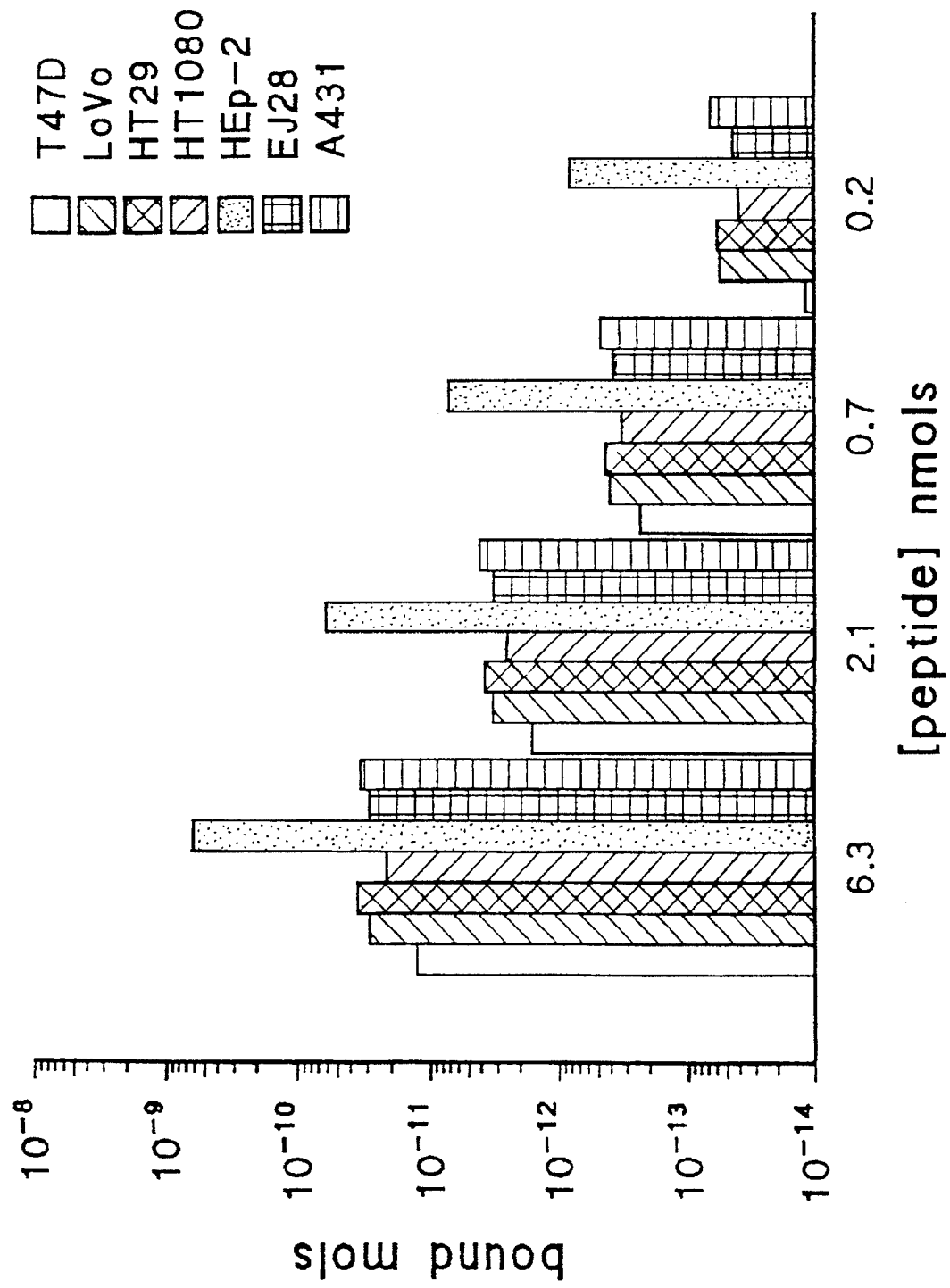
FIG. 3 presents similar data in respect of the radio-labelled peptide $^{125}$I-LDVGGGGSY.

Tumour cells from tumour cell lines T47D, LoVo, HT29, HT1080, HEp-2, EJ28 and A431 were grown to confluence on separate microtitre plates, fixed with glutaraldehyde and then incubated for 1 hour at room temperature with varying concentrations of the three $^{125}$I-labelled peptides $^{125}$I-YLDVY, $^{125}$I-LDVGGGGSY and $^{125}$I-YGGLDVGLDVGGY (SEQ ID NO. 2). The plates were then washed to remove unbound reagent and the cell residues containing the bound label were removed from each well and the residual radioactivity of the bound label measured. From the known level of radioactivity possessed by the radio-labelled peptide, the molar amount of bound peptide was determined. The results are presented in FIGS. 1 to 3.

EXPERIMENT 2

In vivo experiments were performed in nude mice bearing HEp-2 and HT29 tumors obtained by injecting the nude mice subcutaneously in both flanks with from 2 to 5×10$^6$ HEp-2 and HT29 tumor cells and the tumors allowed to grow for three weeks.

In these experiments the nude tumor bearing mice divided into five groups were each injected subcutaneously with the $^{125}$I-labelled peptide $^{125}$I-YGGLDVGLDVGGY (SEQ ID NO. 2).

Figure 4:
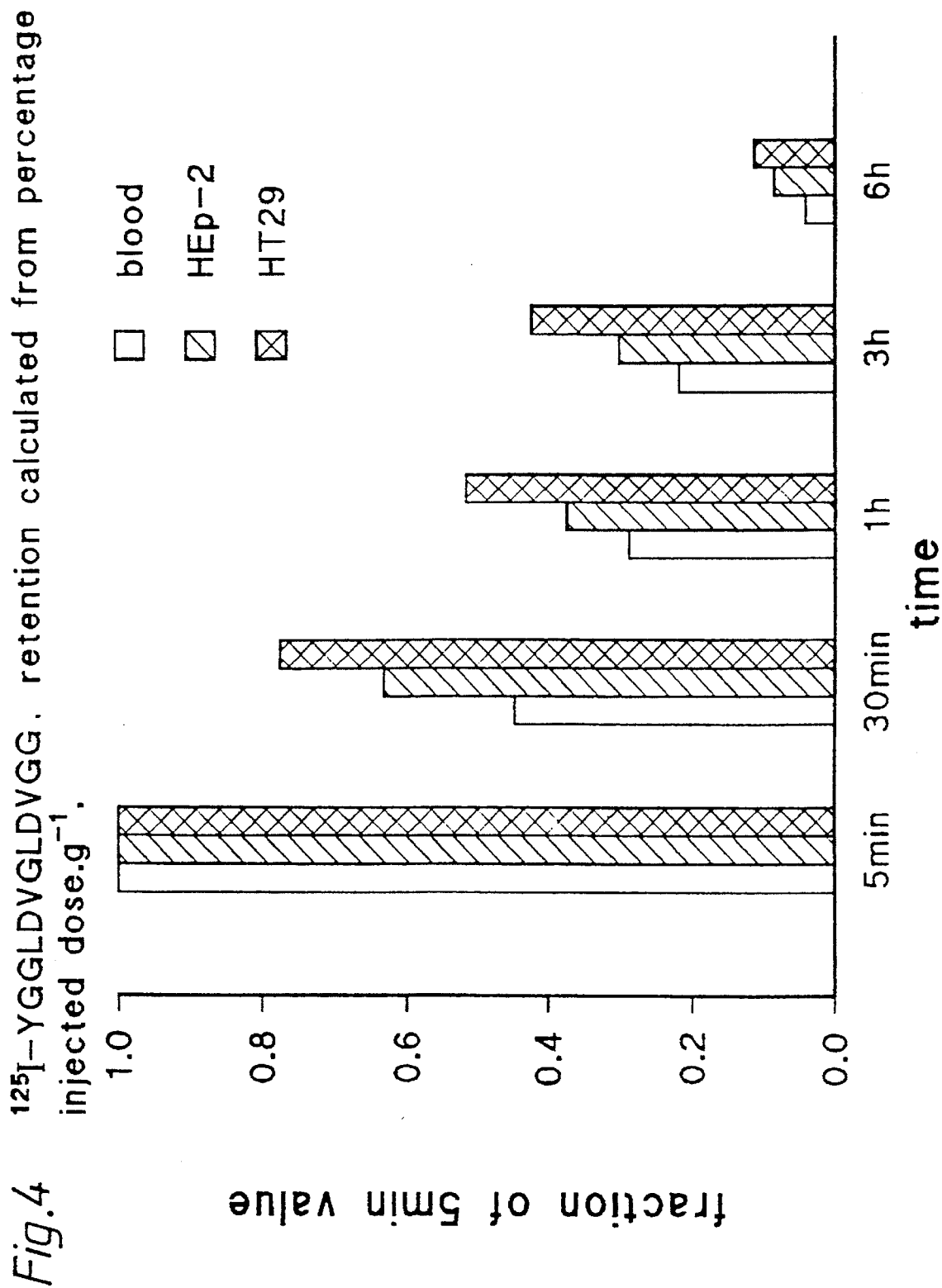
FIG. 4 is a bar chart illustrating the in vivo retention of the radio-labelled peptide $^{125}$I-YGGLDVGLDVGGY (SEQ ID NO. 2) by nude mice bearing HEp-2 and HT29 tumors.

(SEQ ID No. 2), and the uptake of labelled peptide measured against time. For this purpose the five groups were killed at intervals of 5 minutes, 30 minutes, 1 hour, 3 hours, and 6 hours after injection. At this time the blood and tumors were separately removed, weighed and counted for radioactivity, as well as samples taken from all major organs. FIG. 4 shows the retention level at intervals of 30 minutes, 1 hour, 3 hours and 6 hours expressed as a fraction of the percentage injected dose (id) per gram relative to the five minute time point. At this point peptide uptake was 10.3% id per gram in blood, 4.5% id per gram in HEp-2 tumor and 3.0% id per gram in HT29 tumor.

The data presented clearly indicates the capacity of the LDV-containing oligopeptides of this invention to bind to tumor associated LDV binding sites in vivo and therefore potentially to provide useful transport agents for the targeting of imaging and therapeutic reagents onto tumors in vivo. Not only that, but transportation and clearance rates are rapid enabling shortened diagnosis times in the case of tumor imaging and shortened treatment times in the case of tumor therapy.

For diagnostic purposes, the radioactively labelled oligopeptides of this invention are designed for intravenous administration in a suitable liquid carrier at a single dosage rate of no more than about 100 micrograms as a practical upper limit, more usually in the range 10 to 50 µg. For therapeutic purposes, the cytotoxic oligopeptides of this invention, i.e. the LDV-containing carrier peptide conjugated or chemically linked to a cytotoxic agent, such as the ricin A-chain, will usually be employed at dosage rates in the range 1 mg to 1 g depending on tumor size and/or bodyweight, and will usually be administrated serially over a period of time ranging from a few hours to a few days, or in some cases over a period of several weeks. Placing these figures in perspective, and given an average human plasma volume of 2.5 L, a single diagnostic injection of 100 µg represents a maximum peptide plasma concentration of from about 0.078 µM to about 0.15 µM depending on the molecular weight of the peptide, even assuming no clearance of the peptide from the body. Correspondingly, a therapeutic dosage of 1 mg represents a maximum peptide plasma concentration of from about 0.78 µM to about 1.5 µM, again assuming no clearance of peptide from the body. At these extremely low peptide plasma concentration, which in practice will never be attained due to the systemic clearance rates of the peptide from the body, it is highly surprising that any significant amount of LDV peptide remains bound to the tumor, let alone a sufficient amount to permit effective imaging or treatment of the tumor. Those peptide plasma concentrations may indeed be contrasted quite remarkably with the >500 µM concentration recorded by Kloczewiak et al, loc. cit., as necessary to obtain 50% inhibition of fibronectin binding to activated platelets using the peptide HHLQLLKQLLDV (SEQ ID NO. 6) and which figure would indicate a very low level of binding of the LDV-containing peptide to the activated platelets. In contrast to that, the LDV-containing peptides used in the present invention show a quite exceptional and quite unexpected high level of affinity for tumor cells in vivo.

Whether for diagnostic or chemotherapeutic purposes, the labelled or cytotoxic oligopeptides of this invention will be formulated in a suitable liquid carrier for intravenous administration. Suitable carriers for this purpose include physiological saline, sterilized water, various other buffer and/or sugar or salt solutions as known in the art. For convenience of administration the concentration of labelled or cytotoxic peptide in the injectable carrier liquid will usually be in the range 1 to 30% by weight, more usually 1 to 10% by weight.

I claim:

1. An oligopeptide consisting of from 4 to 50 peptide units containing as a triplet therein the amino acid sequence leu-asp-val (LDV) and as a result of which the oligopeptide is capable of binding in vivo with pathological tissues containing an LDV binding site, that oligopeptide having attached thereto or conjugated therewith a radioactive label or cytotoxin.

2. An oligopeptide according to claim 1, which contains from 4 to 30 peptide units.

3. An oligopeptide according to claim 1, comprising as the peptide chain the sequence Asp-Glu-Leu-Pro-Gln-Leu-Val-Thr-Leu-Pro-His-Pro-Leu-Leu-His-Gly-Pro-Glu-Ile-Leu-Asp-Val-Pro-Ser-Thr (DELPQLVTLPHPLLHGPEILDVPST) SEQ ID No. 1, or a sub-sequence thereof having a length of at least four units and which contains the leu-asp-val (LDV) triplet, and to which peptide chain there is attached said radioactive label or cytotoxin.

4. An oligopeptide comprising from 4 to 50 peptide units and containing the pentapeptide tyr-leu-asp-val-tyr, wherein the peptide is attached to a radioactive label or cytotoxin, and wherein the oligopeptide is capable of binding in-vivo with pathological tissues containing an leu-asp-val (LDV) binding site.

5. An oligopeptide comprising from 4 to 50 peptide units and containing the nonapeptide leu-asp-val-gly-gly-gly-gly-ser-tyr, wherein the peptide is attached to a radioactive label or cytotoxin, and wherein the oligopeptide is capable of binding in-vivo with pathological tissues containing an leu-asp-val (LDV) binding site.

6. An oligopeptide comprising the tridecapeptide having the sequence Tyr-Gly-Gly-Leu-Asp-Val-Gly-Leu-Asp-Val-Gly-Gly-Tyr (YGGLDVGLDVGGY) SEQ ID No. 2, wherein the oligopeptide is attached to a radioactive label or cytotoxin and wherein the oligopeptide is capable of binding in-vivo with pathological tissues containing an leu-asp-val (LDV) binding site.

7. An oligopeptide according to claim 1, which is a radio-labelled oligopeptide of 4 to 50 peptide units containing said LDV triplet.

8. An oligopeptide according to claim 7, which is a radioactively labelled oligopeptide comprising the 25 unit sequence SEQ ID No. 1 or a sub-sequence thereof containing at least four units and containing the said LDV triplet, that sequence or sub-sequence being labelled with a radioactive label.

9. An oligopeptide comprising from 4 to 50 peptide units and containing the pentapeptide tyr-leu-asp-val-tyr, wherein the oligopeptide is labelled with a radioactive label, wherein the oligopeptide is capable of binding in-vivo with pathological tissues containing an leu-asp-val (LDV) binding site.

10. An oligopeptide comprising from 4 to 50 peptide units and containing the nonapeptide leu-asp-val-gly-gly-gly-gly-ser-tyr, wherein the oligopeptide is labelled with a radioactive label, and wherein the oligopeptide is capable of binding in-vivo with pathological tissues containing an leu-asp-val (LDV) binding site.

11. An oligopeptide comprising from 4 to 50 peptide units and containing the tridecapeptide SEQ ID No. 2, wherein the oligopeptide is labelled with a radioactive label, and wherein the oligopeptide is capable of binding in-vivo with pathological tissues containing an leu-asp-val (LDV) binding site.

12. The radioactively labelled peptides:

$^{125}$I-{tyr-leu-asp-val-tyr}

$^{125}$I-{leu-asp-val-gly-gly-gly-gly-ser-tyr} and $^{125}$I-{SEQ ID No. 2}.

13. A diagnostic compound for in vivo tumor imaging comprising a radioactively labelled oligopeptide according to claim 1, wherein the label is selected from $^{99m}$Tc, $^{125}$I and $^{111}$In.

14. An anti-tumor therapeutic compound comprising an oligopeptide having from 4 to 50 peptide units and having as a triplet therein the amino acid sequence leu-asp-val (LDV), wherein the oligopeptide is capable of binding in-vivo with pathological tissues containing a leu-asp-val (LDV) binding site and wherein the oligopeptide is chemically linked to or conjugated with a cytotoxin.

15. An anti-tumor therapeutic compound according to claim 14, wherein the cytotoxin is ricin or a ricin derivative.

16. An anti-tumor therapeutic compound according to claim 15, wherein the cytotoxin is the ricin A-chain.

17. An anti-tumor therapeutic compound according to claim 14, wherein the oligopeptide linked to the cytotoxin is selected from the group consisting of:

i) SEQ ID No. 1;

ii) sub-sequences of SEQ ID No. 1 containing at least 4 peptide units and containing the leu-asp-val (LDV) sequence;

iii) the pentapeptide: tyr-leu-asp-val-tyr;

iv) the nonapeptide: leu-asp-val-gly-gly-gly-gly-ser-tyr; and v) the tridecapeptide: SEQ ID No. 2.

18. An anti-tumor therapeutic compound according to claim 17, wherein the said cytotoxin is ricin or a cytotoxic ricin derivative.

19. A diagnostic reagent for in vivo tumor imaging comprising an intravenously administrable liquid carrier containing an effective amount of a radioactively labelled oligopeptide having from 4 to 50 peptide units and having as a triplet the therein the amino acid sequence leu-asp-val (LDV), wherein the oligopeptide is capable of binding in-vivo with pathological tissues containing a leu-asp-val (LDV) binding site.

20. A diagnostic reagent according to claim 19, wherein the radioactively labelled oligopeptide is an oligopeptide comprising the pentapeptide tyr-leu-asp-val-tyr.

21. A diagnostic reagent according to claim 19, wherein the radioactively labelled oligopeptide is an oligopeptide comprising the pentapeptide tyr-leu-asp-val-tyr.

22. A diagnostic reagent according to claim 19, wherein the radioactively labelled oligopeptide is an oligopeptide comprising the nonapeptide leu-asp-val-gly-gly-gly-gly-ser-tyr.

23. A diagnostic reagent according to claim 19, wherein the radioactively labelled oligopeptide is an oligopeptide comprising the tridecapeptide SEQ ID No. 2.

24. A diagnostic reagent according to claim 19, wherein the radioactively labelled oligopeptide is an oligopeptide selected from the group consisting of $^{125}$I-(tyr-leu-asp-val-tyr), $^{125}$I-(leu-asp-val-gly-gly-gly-gly-ser-tyr), and $^{125}$I-(tyr-gly-gly-leu-asp-val-gly-leu-asp-val-gly-gly-tyr).

25. An anti-tumor therapeutic reagent comprising an intravenously administrable liquid carrier comprising an effective amount of a cytotoxic oligopeptide having from 4 to 50 peptide units and having as a triplet therein the amino acid sequence leu-asp-val (LDV), wherein the oligopeptide is capable of binding in-vivo with pathological tissue containing leu-asp-val (LDV) binding sites, and wherein the oligopeptide is chemically linked to or conjugated with a cytotoxin.

26. An anti-tumor therapeutic reagent according to claim 25, wherein the cytotoxin is ricin or a ricin derivative.

27. An anti-tumor therapeutic reagent according to claim 25, wherein the cytotoxin is ricin A-chain.

28. An anti-tumor therapeutic reagent according to claim 25, wherein the cytotoxic oligopeptide is selected from the group consisting of i) SEQ ID No. 1; ii) sub-sequences of SEQ ID No. 1 containing at least 4 peptide units and containing the leu-asp-val (LDV) sequence; iii) the pentapeptide: tyr-leu-asp-val-tyr; iv) the nonapeptide: leu-asp-val-gly-gly-gly-gly-ser-tyr; and, v) the tridecapeptide: SEQ ID No. 2.

29. An anti-tumor therapeutic reagent according to claim 25, wherein the cytotoxic oligopeptide is selected from the group consisting of i) SEQ ID No. 1; ii) sub-sequences of SEQ ID No. 1 containing at least 4 peptide units and containing the leu-asp-val (LDV) sequence; iii) the pentapeptide: tyr-leu-asp-val-tyr; iv) the nonapeptide: leu-asp-val-gly-gly-gly-gly-ser-tyr; and v) the tridecapeptide: SEQ ID No. 2; and wherein the cytotoxin is ricin or cytotoxic ricin derivative.

30. A method of in vivo tumor imaging which comprises intravenously administering to the patient an effective amount of a radioactively labelled oligopeptide having from 4 to 50 peptide units and having as a triplet therein the amino acid sequence leu-asp-val (LDV), wherein the oligopeptide is capable of binding in-vivo with pathological tissues containing a leu-asp-val (LDV) binding site and radiographically detecting the bound label.

31. A method of treating tumors in vivo which comprises intravenously administering to the patient an effective amount of a cytotoxic oligopeptide having from 4 to 50 peptide units and having as a triplet therein the amino acid sequence leu-asp-val (LDV), wherein the oligopeptide is capable of binding in-vivo with pathological tissues containing a leu-asp-val (LDV) binding site and wherein the oligopeptide is attached or conjugated with a cytotoxin.

* * * * *